US008155890B2

(12) United States Patent
Goto et al.

(10) Patent No.: US 8,155,890 B2
(45) Date of Patent: Apr. 10, 2012

(54) EXHAUST GAS ANALYSIS METHOD AND EXHAUST GAS ANALYSIS APPARATUS

(75) Inventors: Katsutoshi Goto, Okazaki (JP);
Masahiro Yamakage, Anjo (JP);
Tomoyasu Iwase, Aichi (JP); Tokio Okano, Toyota (JP); Yoshihiro Deguchi, Yokohama (JP); Masanobu Mizoguchi, Yokohama (JP); Atushi Takita, Yokohama (JP); Norihiro Fukuda, Nagasaki (JP)

(73) Assignees: Toyota Jidosha Kabushiki Kaisha, Toyota-shi, Aichi-ken (JP); Mitsubishi Heavy Industries, Ltd., Tokyo (JP)

( * ) Notice: Subject to any disclaimer, the term of this patent is extended or adjusted under 35 U.S.C. 154(b) by 602 days.

(21) Appl. No.: 12/083,521

(22) PCT Filed: Dec. 15, 2006

(86) PCT No.: PCT/JP2006/325566
§ 371 (c)(1),
(2), (4) Date: Apr. 11, 2008

(87) PCT Pub. No.: WO2007/069786
PCT Pub. Date: Jun. 21, 2007

(65) Prior Publication Data
US 2009/0164138 A1 Jun. 25, 2009

(30) Foreign Application Priority Data

Dec. 16, 2005 (JP) ................. 2005-363400

(51) Int. Cl.
*G01N 31/10* (2006.01)
*G01N 31/12* (2006.01)
*G01R 23/18* (2006.01)
*G01J 3/28* (2006.01)
*G01J 5/02* (2006.01)

(52) U.S. Cl. .............. 702/24; 702/32; 702/66; 356/438; 250/339.13

(58) Field of Classification Search .............. 702/22–24, 702/30, 32, 33, 40, 57, 66, 76, 71, 98, 99, 702/105, 130, 134, 138, 179; 73/19.02, 19.05, 73/1.02, 1.06, 114.77, 23.21–23.27, 23.35–23.37, 73/31.04, 35.03, 35.04, 35.06, 35.12; 250/351, 250/345, 339.04, 339.07, 370.15, 390.07, 250/251.1, 339.01, 338.5, 339.09, 338.1, 250/339.11–339.14; 324/601, 318; 356/438; 701/29, 101, 108, 109
See application file for complete search history.

(56) References Cited

U.S. PATENT DOCUMENTS
3,958,122 A * 5/1976 Jowett et al. ............... 250/346
(Continued)

FOREIGN PATENT DOCUMENTS
JP 5-77023 10/1993
(Continued)

OTHER PUBLICATIONS
Supplementary European Search Report dated May 11, 2009.
(Continued)

*Primary Examiner* — Michael Nghiem
*Assistant Examiner* — Ricky Ngon
(74) *Attorney, Agent, or Firm* — Finnegan, Henderson, Farabow, Garrett & Dunner, LLP

(57) ABSTRACT

An exhaust gas analysis method comprises applying a laser beam to the exhaust gas discharged from an internal combustion engine, receiving the laser beam that has passed through the exhaust gas, and measuring the concentration of any of the components contained in the exhaust gas based on the received laser beam. The exhaust gas analysis method further comprises detecting the absorption spectrum of the laser beam absorbed in the exhaust gas by using the received laser beam, calculating the concentration of the specific gas component by using the absorption spectrum, calculating the temperature of the exhaust gas by using the absorption spectrum, calculating the pressure of the exhaust gas by using the absorption spectrum, correcting the calculated concentration of the component contained in the exhaust gas by using the calculated temperature, correcting the concentration by using the calculated pressure, and outputting the true concentration value.

5 Claims, 10 Drawing Sheets

U.S. PATENT DOCUMENTS

| | | | |
|---|---|---|---|
| 5,185,645 A | | 2/1993 | Sartorius et al. |
| 5,381,010 A | | 1/1995 | Gordon |
| 5,418,366 A | * | 5/1995 | Rubin et al. ............... 250/338.5 |
| 5,572,031 A | | 11/1996 | Cooper |
| 5,585,636 A | | 12/1996 | Dollansky |
| 5,838,008 A | * | 11/1998 | Esler et al. ............... 250/339.08 |
| 6,147,351 A | * | 11/2000 | Huiku ........................... 250/343 |
| 6,150,661 A | | 11/2000 | McCaul |
| 6,615,142 B1 | * | 9/2003 | Hovde .............................. 702/30 |
| 2006/0082778 A1 | * | 4/2006 | Paldus et al. .................. 356/437 |
| 2009/0039284 A1 | | 2/2009 | Goto et al. |

FOREIGN PATENT DOCUMENTS

| | | |
|---|---|---|
| JP | 6-148072 | 5/1994 |
| JP | 8-338805 | 12/1996 |
| JP | 2837442 | 10/1998 |
| JP | 2000-206041 | 7/2000 |
| JP | 2000-283915 | 10/2000 |
| JP | 2001-174410 | 6/2001 |
| JP | 2004-117259 | 4/2004 |
| JP | 2006-184180 | 7/2006 |
| WO | WO 2005/077001 A2 | 8/2005 |
| WO | WO 2005/077001 A3 | 8/2005 |
| WO | WO 2005/111585 A2 | 11/2005 |
| WO | WO 2005/111585 A3 | 11/2005 |

OTHER PUBLICATIONS

Office Action from the U.S. Patent and Trademark Office for U.S. Appl. No. 12/309,584 dated Feb. 4, 2011.

Extended Search Report for EP Application No. 07806294 dated Aug. 22, 2011.

* cited by examiner

EXHAUST GAS ANALYSIS METHOD AND EXHAUST GAS ANALYSIS APPARATUS

TECHNICAL FIELD

The present invention relates to a method for analyzing an exhaust gas discharged from an internal combustion engine of an automobile or the like and an exhaust gas analysis apparatus, and particularly to an exhaust gas analysis method and an exhaust gas analysis apparatus for calculating, measuring, and analyzing the concentrations, temperatures, and the like of the components contained in an exhaust gas in an accurate, real-time manner.

BACKGROUND ART

As a conventional exhaust gas analysis apparatus of this type, JP Patent Publication (Kokai) No. 2004-117259 discloses an in-vehicle HC measurement apparatus. The in-vehicle HC measurement apparatus includes the following in-vehicle components: an NDIR (non-dispersive infrared spectroscopy) gas analyzer for continuously measuring the HC (hydrocarbon) concentration in the exhaust gas flowing through the exhaust duct connected to the engine, an exhaust gas flowmeter for continuously measuring the flow of the exhaust gas flowing through the exhaust duct, and an arithmetic processing circuit for computing the outputs of the NDIR gas analyzer and the exhaust gas flowmeter to continuously calculate the amount of THC (total hydrocarbon) in the exhaust gas.

When infrared laser beam-based measurement (infrared absorption method) is applied to the exhaust gas tube, the following problem arises. That is, in this measurement method, the shape of the laser beam absorption spectrum is used to compute and determine the exhaust gas concentration in the tube. On the other hand, the pressure and the concentration in the exhaust gas tube will abruptly change depending on how the engine is operated. When the pressure varies, a phenomenon called broadening changes the shape of the laser beam absorption spectrum, so that the determined concentration value becomes inaccurate.

DISCLOSURE OF THE INVENTION

The concentration of any of the gas components present in the exhaust gas determined by the shape of the absorption spectrum vary with the pressure and temperature. To obtain accurate concentration values, it is therefore necessary to measure the pressure of the exhaust gas. A pressure gauge is typically provided to measure the pressure. In this case, however, the system becomes complicated partly because the number of parts increases. To address this problem, it is necessary to measure the exhaust gas pressure in the tube in real-time, so that the shape of the absorption spectrum and hence the concentration are corrected. In this process, the calculation for determining the concentration using the shape of the absorption spectrum as a parameter requires repetitive calculation, resulting in increase in analysis time and hence difficulty performing real-time measurement.

The present invention has been made in view of such a problem. An object of the present invention is to provide an exhaust gas analysis method and an exhaust gas analysis apparatus substantially insensitive to variation in pressure and temperature of the exhaust gas and capable of calculating, measuring, and analyzing the concentration of any of the components contained in the exhaust gas in an accurate, real-time manner.

To achieve the above object, the exhaust gas analysis method according to the present invention includes applying a laser beam to the exhaust gas discharged from an internal combustion engine, receiving the laser beam that has passed through the exhaust gas, and measuring the concentration of any of the components contained in the exhaust gas based on the received laser beam. The method is characterized in that the method further includes detecting the absorption spectrum of the laser beam absorbed in the exhaust gas by using the received laser beam, calculating the concentration of the component contained in the exhaust gas, the temperature of the exhaust gas, and the pressure of the exhaust gas by using the absorption spectrum, and correcting the concentration of the component contained in the exhaust gas by using the calculated exhaust gas temperature and exhaust gas pressure.

In the thus configured exhaust gas analysis method of the present invention, the laser beam received after passing through the exhaust gas discharged from the internal combustion engine is used to detect the absorption spectrum absorbed in the exhaust gas, and the concentration of a specific gas component contained in the exhaust gas, such as carbon monoxide and nitrogen oxide, is calculated based on the amount of attenuation in the absorption spectrum, that is, the ratio of the intensity of the light that has passed through the exhaust gas to the intensity of the light that has not passed through the exhaust gas. Then, the absorption spectrum is used to calculate the exhaust gas temperature and the exhaust gas pressure, and the calculated exhaust gas temperature and exhaust gas pressure are used to correct the calculated concentration of the component. It is therefore possible to obtain the concentration of the component with high measurement accuracy and a high degree of fidelity to the changes in pressure and temperature in the exhaust gas passage. As a result, accurate analysis can be performed. Further, the ability to calculate the pressure without using a pressure gauge allows realtime measurement, a simplified configuration, and cost reduction.

Another aspect of the exhaust gas analysis method according to the present invention includes applying a laser beam to the exhaust gas discharged from an internal combustion engine, receiving the laser beam that has passed through the exhaust gas, and measuring the concentration of any of the components contained in the exhaust gas based on the received laser beam. The method is characterized in that the method further includes detecting the absorption spectrum of the laser beam absorbed in the exhaust gas by using the received laser beam, calculating the concentration of the component contained in the exhaust gas, the temperature of the exhaust gas, and the pressure of the exhaust gas by using the absorption spectrum, calculating a concentration correction value based on not only the theoretical spectrum determined by the exhaust gas temperature, the exhaust gas pressure, and the concentration of the component contained in the exhaust gas that have been calculated from the absorption spectrum but also the detected absorption spectrum, and correcting the calculated concentration of the component contained in the exhaust gas by using the correction value.

Specifically, the theoretical spectrum is superimposed on the absorption spectrum to calculate a first integral (first area) by integrating the theoretical spectrum, a second integral (second area) of the portion where the value of one of the spectra is larger than that of the other spectrum, and a third integral (third area) of the portion where the value of the other spectrum is larger than that of the one spectrum. Then, the correction value is calculated by using the following equation: (First integral−Second integral+Third integral)/First integral, and the calculated concentration (first area) is multiplied by the correction value for correction.

In the thus configured exhaust gas analysis method, the theoretical spectrum uniquely determined by the calculated exhaust gas temperature, exhaust gas pressure, and concentration of the component contained in the exhaust gas is compared with the detected absorption spectrum, and the concentration correction value can be obtained based on the two spectra. Specifically, the correction value can be obtained by calculating the areas defined by the two spectra. Then, the calculated concentration is multiplied by the correction value to provide an accurate concentration of the specific component of the exhaust gas. As a result, accurate exhaust gas analysis can be performed.

A specific preferred aspect of the exhaust gas analysis method according to the present invention is characterized in that calculating the concentration of the component contained in the exhaust gas comprises preparing a plurality of spectrum patterns obtained by changing the theoretical spectrum of the specific component of the exhaust gas to be analyzed according to the exhaust gas concentration, and calculating the concentration from the exhaust gas concentration for the nearest approximate spectrum pattern. In this configuration, for example, the concentration can be calculated by selecting the absorption spectrum pattern most approximate to a plurality of spectrum patterns obtained by changing the theoretical water vapor spectrum according to the exhaust gas concentration, and determining the concentration from the exhaust gas concentration for the nearest approximate absorption spectrum pattern.

In the exhaust gas analysis method according to the present invention, the exhaust gas temperature is preferably calculated from the ratio between the transmitted light intensities at at least two wavelengths selected from the absorption spectrum for $H_2O$. In this configuration, since the temperature can be calculated by using $H_2O$ always present in the exhaust path through which the exhaust gas flows, the temperature can be measured accurately. As a result, accurate exhaust gas analysis can be performed.

Further, in the exhaust gas analysis method according to the present invention, the exhaust gas pressure is preferably calculated based on the spectrum width at the peak wavelength in the absorption spectrum for $H_2O$. Specifically, the pressure is determined by detecting the spectrum width at half the peak value at the peak wavelength in the absorption spectrum, correcting the detected spectrum width by using the calculated temperature, and calculating the pressure by using the corrected spectrum width. In this configuration, by using $H_2O$ always present in the exhaust path, the pressure can be easily calculated in an accurate manner from the spectrum width at the peak wavelength in the $H_2O$ absorption spectrum.

The exhaust gas analysis apparatus according to the present invention is an apparatus that applies a laser beam generated in laser beam generation means to the exhaust gas discharged from an internal combustion engine, receives the laser beam that has passed through the exhaust gas, and measures the concentration of any of the components contained in the exhaust gas based on the received laser beam. The exhaust gas analysis apparatus is characterized in that the apparatus comprises detection means for detecting the absorption spectrum of the laser beam absorbed in the exhaust gas by using the received laser beam, calculation means for calculating the concentration of the component contained in the exhaust gas, the temperature of the exhaust gas, and the pressure of the exhaust gas by using the absorption spectrum, and correction means for correcting the calculated concentration of the component contained in the exhaust gas by using the calculated exhaust gas temperature and exhaust gas pressure.

The thus configured exhaust gas analysis apparatus applies the laser beam to the exhaust gas, receives the transmitted light, and uses the received laser beam to detect the absorption spectrum of the laser beam absorbed in the exhaust gas. Then, since the absorption spectrum is used to calculate the concentration of the component contained in the exhaust gas, the temperature of the exhaust gas and the pressure of the exhaust gas, and the calculated exhaust gas temperature and exhaust gas pressure are used to correct the calculated concentration of the component, it is possible to calculate the true concentration of the component contained in the exhaust gas without being affected by the variation in pressure and temperature. As a result, accurate exhaust gas analysis can be performed.

Another aspect of the exhaust gas analysis apparatus according to the present invention is an apparatus that applies a laser beam generated in laser beam generation means to the exhaust gas discharged from an internal combustion engine, receives the laser beam that has passed through the exhaust gas, and measures the concentration of any of the components contained in the exhaust gas based on the received laser beam. The exhaust gas analysis apparatus is characterized in that the apparatus comprises detection means for detecting the absorption spectrum of the laser beam absorbed in the exhaust gas by using the received laser beam, calculation means for calculating the concentration of the component contained in the exhaust gas, the temperature of the exhaust gas, and the pressure of the exhaust gas by using the absorption spectrum, the calculation means further calculating a concentration correction value based on not only the theoretical spectrum determined by the calculated exhaust gas temperature, exhaust gas pressure, and concentration of the component of the exhaust gas but also the detected absorption spectrum, and correction means for correcting the calculated concentration of the component contained in the exhaust gas by using the correction value.

The thus configured exhaust gas analysis apparatus applies the laser beam to the exhaust gas, receives the transmitted light, and uses the received laser beam to detect the absorption spectrum of the laser beam absorbed in the exhaust gas. Since the absorption spectrum is used to calculate the concentration of the component contained in the exhaust gas, the temperature of the exhaust gas and the pressure of the exhaust gas, and the concentration correction value is further calculated based on not only the theoretical spectrum determined by the calculated exhaust gas temperature, exhaust gas pressure, and concentration of the component of the exhaust gas but also the detected absorption spectrum, and the correction value is used to correct the calculated concentration of the component contained in the exhaust gas, it is possible to calculate the concentration without being affected by the variation in pressure and temperature. As a result, accurate exhaust gas analysis can be performed.

According to the exhaust gas analysis method and the exhaust gas analysis apparatus of the present invention, when the exhaust gas is analyzed by sending the laser beam through the exhaust gas and using the absorption spectrum of the laser beam that has passed through the exhaust gas to calculate the gas concentration of a specific component in the exhaust gas, temperature-dependent and pressure-dependent errors in the calculated gas concentration can be corrected in real-time. As a result, an accurate gas concentration value can be calculated, measured, and analyzed. Further, since the shape of the absorption spectrum is used to calculate the pressure in the pressure detection process, no pressure gauge is necessary, so that the apparatus configuration can be simplified and the pressure measurement can be performed quickly.

BRIEF DESCRIPTION OF THE DRAWINGS

FIG. 9(a) is a correction diagram showing the amount of line width correction versus temperature (K), FIG. 9(b) is a correction diagram showing line width versus pressure (MPa), and FIG. 9(c) is a correction diagram showing the amount of line width correction versus $H_2O$ concentration in another embodiment;

Figure 1:
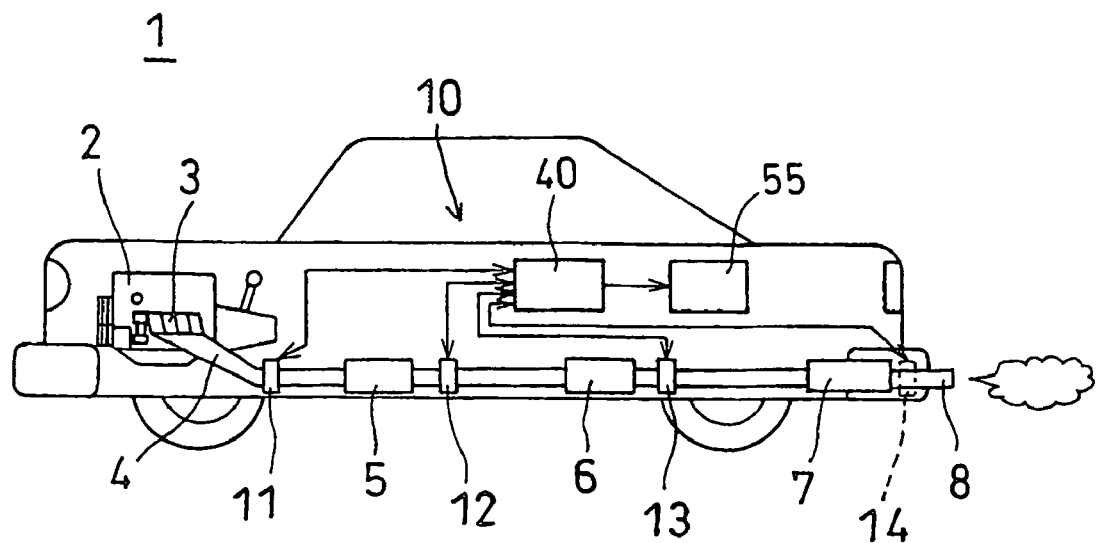
FIG. 1 is a key component configuration diagram of an embodiment of the exhaust gas analysis apparatus according to the present invention implemented in a vehicle.

Reference numerals in the drawings are summarized as follows: Reference numeral 1 denotes an automobile. Reference numeral 1A denotes an engine bench. Reference numeral 2 denotes an engine (internal combustion engine). Reference numeral 3 denotes an exhaust manifold (exhaust path). Reference numeral 4 denotes an exhaust duct (exhaust path). Reference numeral 5 denotes a first catalytic converter (exhaust path). Reference numeral 6 denotes a second catalytic converter (exhaust path). Reference numeral 7 denotes a muffler (exhaust path). Reference numeral 8 denotes an exhaust pipe (exhaust path). Reference numeral 10 denotes an exhaust gas analysis apparatus (gas analysis apparatus). Reference numerals 11 to 14 denote sensor units. Reference numeral 20 denotes a sensor base. Reference numeral 21 denotes an exhaust gas venthole. Reference numeral 23 denotes a sensor hole (illumination light venthole). Reference numeral 24 denotes a sensor hole (illumination light venthole). Reference numeral 25 denotes an optical fiber (illuminator). Reference numeral 26 denotes a detector (light detector). Reference numerals 30 and 31 denote mirrors. Reference numeral 38 denotes a light venthole. Reference numeral 39 denotes a slit (light venthole). Reference numeral 40 denotes a laser oscillation/light reception controller. Reference numeral 43 denotes a demultiplexer. Reference numerals 44A to 44C denote demultiplexers. Reference numerals 45A to 45C and 46A to 46C denote multiplexers. Reference numerals 50A to 50C denote differential optical detectors (detection means). Reference numeral 55 denotes a personal computer (signal analysis apparatus, calculation means, and correction means). Reference character R denotes a laser beam.

BEST MODE FOR CARRYING OUT THE INVENTION

An embodiment in which the gas analysis apparatus according to the present invention is applied to an exhaust gas analysis apparatus for an automobile will be described below in detail with reference to the drawings.

Figure 2:
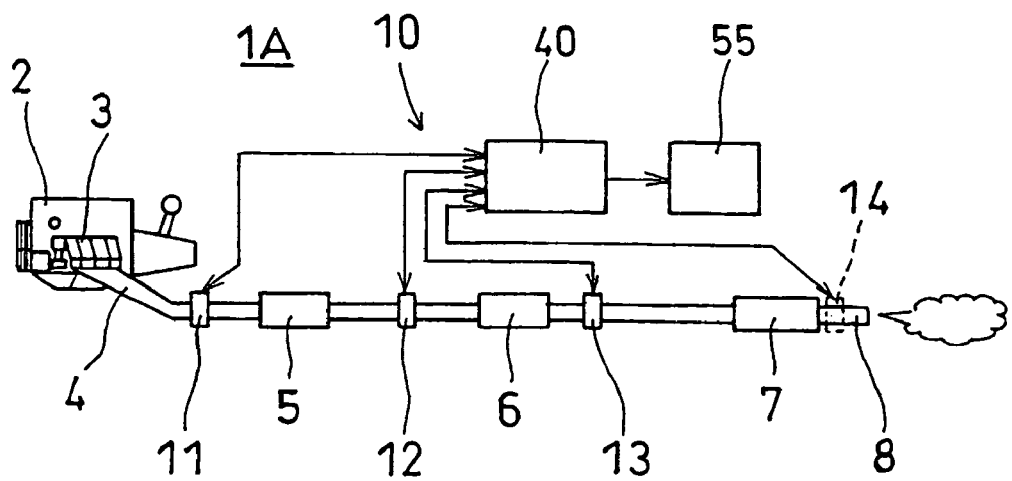
FIG. 2 is a key component configuration diagram of another embodiment of the exhaust gas analysis apparatus according to the present invention mounted on an engine bench.
Figure 3:
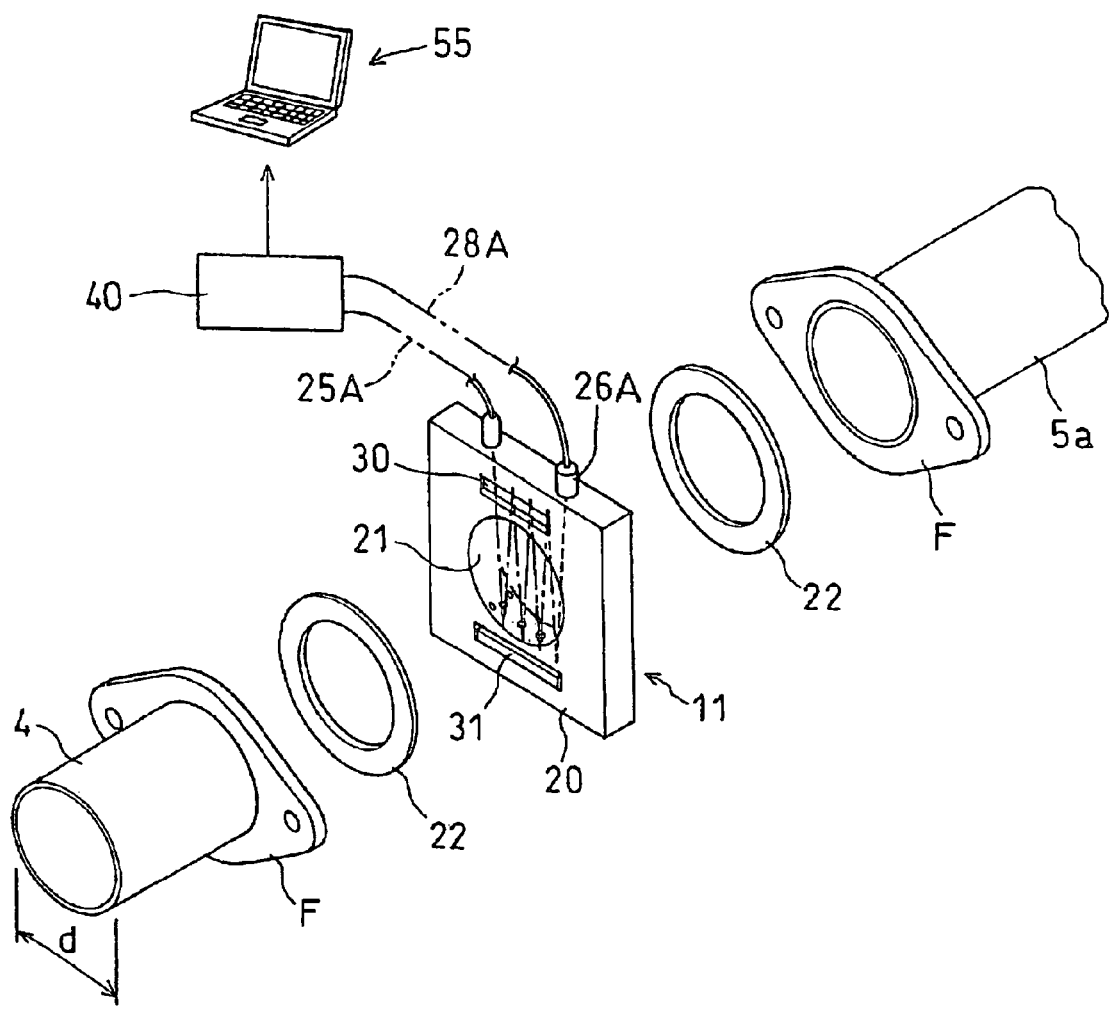
FIG. 3 is a key component configuration diagram of the exhaust gas analysis apparatus, including an exploded perspective view of the key components of one sensor unit.

FIG. 1 is a key component configuration diagram of the exhaust gas analysis apparatus according to the present invention implemented in an automobile. FIG. 2 is a key component configuration diagram of the exhaust gas analysis apparatus in FIG. 1 mounted on an engine bench. FIG. 3 is a key component configuration diagram of the exhaust gas analysis apparatus, including an exploded perspective view of the key components of a sensor unit. FIGS. 4(a) to 4(d) are a partial cross-sectional front view showing the details of the sensor unit in FIG. 3, the cross-sectional view taken along the line A-A, the cross-sectional view taken along the line B-B, and the key component cross-sectional view taken along the line C-C, respectively. FIG. 5 is a block diagram showing the whole configuration of the exhaust gas analysis apparatus including the key component configuration of a laser oscillation/light reception controller and a signal analysis apparatus.

In FIGS. 1 to 5, the exhaust gas analysis apparatus of this embodiment is an apparatus that analyzes the exhaust gas, as a gas to be analyzed, discharged from the engine (internal combustion engine) 2 disposed in the automobile 1. Alternatively, as shown in FIG. 2, the exhaust gas analysis apparatus is an apparatus that analyzes the exhaust gas from the engine 2 mounted on the engine bench 1A. The exhaust gas flows discharged from the cylinders of the engine 2 are merged in the exhaust manifold 3, introduced into the first catalytic converter 5 through the exhaust duct 4, further introduced into the second catalytic converter 6, and discharged through the muffler 7 and the exhaust pipe 8 to the atmosphere. The exhaust path that forms the passage (path) through which the exhaust gas flows is formed of the exhaust manifold 3, the exhaust duct 4, the first catalytic converter 5, the second catalytic converter 6, the muffler 7, and the exhaust pipe 8. The two catalytic converters 5 and 6 clean the exhaust gas discharged from the engine 2, and the muffler 7 muffles the noise and reduces the pressure. The resultant exhaust gas is then discharged to the atmosphere. The muffler may be formed of two components: a primary muffler and a secondary muffler.

The plurality of members that form the exhaust path are connected with bolts or the like in such a way that the flanges of the members abut each other. For example, exhaust pipes are connected to the upstream and downstream sides of the larger-diameter body of each of the first and second catalytic converters 5 and 6, and both ends of the exhaust pipe have flanges F, F welded or otherwise joined thereto. Similarly, exhaust pipes are connected to the upstream and downstream sides of the larger-diameter body of the muffler 7, and both ends of the exhaust pipe have flange F, F joined thereto. The terminal exhaust pipe 8 is directly welded or otherwise joined to the muffler 7. The plurality of members that form the exhaust path are thus connected via the flanges, and form a circular cross-sectional shape having a diameter d, through which the exhaust gas passes.

The exhaust gas analysis apparatus 10 of this embodiment includes a plurality of sensor units 11 to 14 disposed at a plurality of locations along the exhaust path. The first sensor unit 11 is disposed between the first catalytic converter 5 and the engine-side exhaust duct 4 upstream of the first catalytic converter 5. The second sensor unit 12 is disposed downstream of the first catalytic converter 5, and the third sensor unit 13 is disposed downstream of the second catalytic converter 6. The fourth sensor unit 14 is disposed in the exhaust pipe 8 downstream of the muffler 7. The sensor unit 14 may be disposed somewhere along the exhaust pipe, or may be inserted into the opening at the end of the exhaust pipe. A sensor unit may also be disposed in the exhaust duct for each of the cylinders, upstream of the first sensor unit 11, before the exhaust ducts are merged in the exhaust manifold 3.

The exhaust duct 4, the first catalytic converter 5, the second catalytic converter 6, and the muffler 7 are connected by tightening the respective flanges F, F with bolts, and the sensor units 11, 12, and 13 disposed between the exhaust path forming members are sandwiched between the respective flanges F, F. The flanges F, F are formed at both ends of each of the exhaust path forming members, and the joint surfaces of the flanges are perpendicular to the center line of the exhaust path. As a result, each of the sensor units 11 to 13 is sandwiched between the flanges F, F and transversely disposed across the exhaust path. The fourth sensor unit 14, which analyzes the exhaust gas immediately before it is discharged to the atmosphere, may be sandwiched between the flanges F, F in the intermediate portion of the exhaust pipe 8 jutting out from the muffler 7. The number of sensor units to be disposed may be arbitrary set.

The sensor units 11 to 14 are identically configured. Accordingly, one sensor unit 11 will be described with reference to FIGS. 3 and 4. The sensor unit 11 has the sensor base 20 formed of a rectangular thin plate. At the center of the sensor base, there is formed the exhaust gas venthole 21 having the same diameter d as the inner diameter d of the circular cross-sectional exhaust pipe, and the exhaust gas passes through the exhaust gas venthole. The thickness of the plate-like sensor base 20 is preferably as thin as possible to the extent that the sensor base 20 can secure the laser beam illuminator and the laser beam receiver. Specifically, the thickness of the sensor base 20 preferably ranges, for example, from approximately 5 mm to 20 mm. Thicknesses greater than 20 mm likely make the exhaust gas flow turbulent, while thicknesses smaller than 5 mm complicate the attachment of the measurement laser beam illuminator and the light detector for receiving the laser beam transmitted through the exhaust gas. The sensor base 20 can be easily disposed as required at an arbitrary location along the exhaust path. It is noted that the thickness of the sensor base 20 can be arbitrarily set.

As described above, not only is the shape of the exhaust gas venthole 21 formed in the sensor base 20 a circle having the same diameter as the inner diameter of the exhaust pipe so that the exhaust gas flow will not become turbulent, but also the sensor base 20 is thin. The sensor units 11 to 14 attached along the exhaust path will thus not make the exhaust gas flow turbulent but allow smooth exhaust with less pressure loss. When the nominal diameter d of the exhaust gas venthole 21 is, for example, 30 mm, the actual diameter is preferably 30±1 to 2 mm because such a difference in diameter will not likely make the exhaust gas flow turbulent. Such a diameter range preferably provides substantially the same cross-sectional shape. Although the sensor base 20 is typically formed of a metal plate or a ceramic plate, the material of the sensor base 20 is not particularly limited to specific ones.

The sensor base 20 is sandwiched between the flanges F, F and secured with bolts and nuts or the like (not shown), with gaskets 22, 22 provided on both sides of the sensor base 20 sandwiched between the flange F, F and the sensor base 20. The gasket 22 is made of, for example, asbestos, and has an exhaust gas venthole having the same diameter as the inner diameter of the exhaust duct. In such a configuration, even when the connected exhaust path includes the sensor base 20 sandwiched between the flanges F, F, no exhaust gas will leak somewhere along the exhaust path and the extra length added to the exhaust path is small. FIG. 3 shows a configuration in which the sensor base 20 and the gaskets 22, 22 on both sides thereof are secured between the flange F welded to the downstream end of the exhaust duct 4 and the flange F welded to the end of the exhaust pipe 5a upstream of the catalytic converter 5.

The sensor base 20 has two sensor holes 23 and 24 that pass through the center part of the plate thickness from the end surface to the exhaust gas venthole. The sensor hole 23 communicates with the exhaust gas venthole 21 and forms an illumination light venthole through which the illumination laser beam can reach the light detector across the exhaust gas venthole 21. The sensor hole 24 communicates with the exhaust gas venthole 21 and forms a transmitted light venthole through which the laser beam can reach the light detector. The communicating sensor holes 23 and 24 are perpendicular to the exhaust gas flowing direction.

The sensor unit 11 is configured in such a way that an optical fiber 25A, serving as the illuminator that emits the laser beam, is secured in the sensor hole 23 and a detector 26A, serving as the light detector that receives the laser beam that has exited from the optical fiber 25A and passed through the exhaust gas present in the exhaust gas venthole 21, is secured in the sensor hole 24. That is, the sensor unit 11 is configured in such a way that the laser beam emitted from the illumination-side optical fiber 25A across the exhaust path is reflected off the two mirrors 30 and 31, attenuated through the exhaust gas, and received by the detector 26A. The mirrors reflect the illumination laser beam and guide it to the detector.

The sensor hole 23 forms the illumination light venthole, which connects the exhaust gas venthole 21 to the illuminating optical fiber 25, and through which the measurement laser beam emitted from the optical fiber passes as described above. The sensor hole 24 forms the transmitted light venthole, which connects the exhaust gas venthole 21 to the light receiving detector 26, and through which the laser beam that has passed through the exhaust gas reaches the detector 26. The inner circumferential surface of the sensor hole 23 preferably has scattered laser beam elimination means. As the scattered light elimination means, a female thread is preferably formed in the inner circumferential surface of the sensor hole. The female thread can easily be formed by tapping a through hole.

Figure 4:
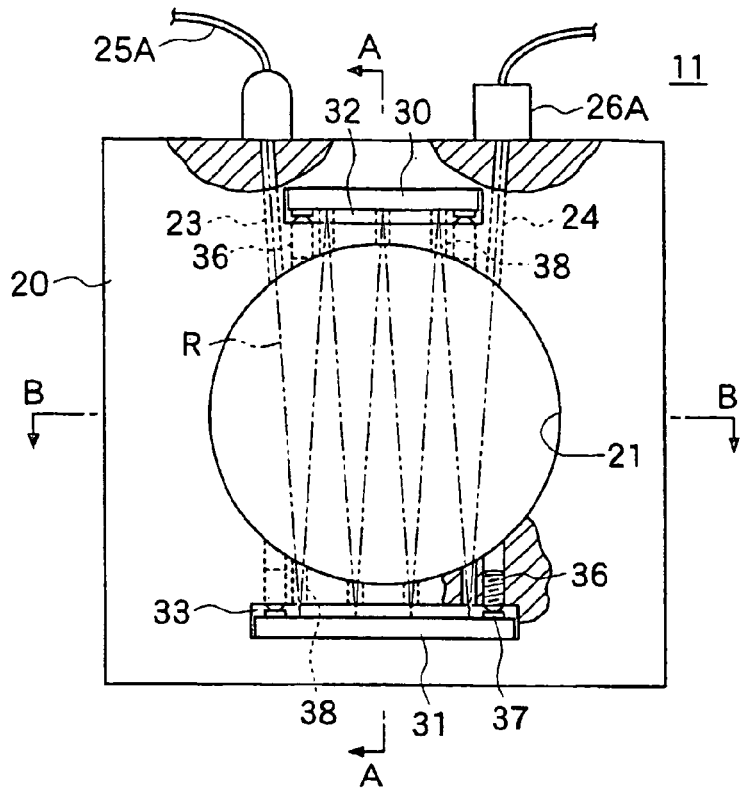
FIG. 4(a) is the front view of the sensor unit in FIG. 3.
FIG. 4(b) is the cross-sectional view taken along the line A-A shown in FIG. 4(a)
FIG. 4(c) is the cross-sectional view taken along the line B-B shown in FIG. 4(a)
FIG. 4(d) is the key component cross-sectional view taken along the line C-C shown in FIG. 4(c)
Figure 4:
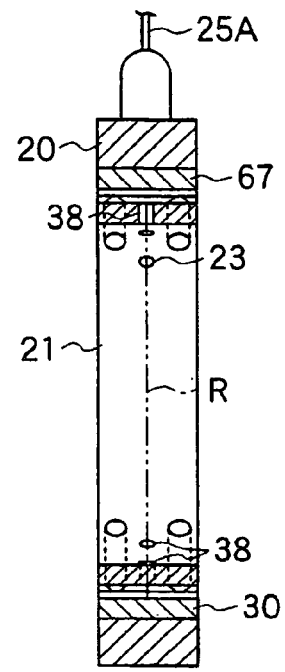
Figure 4:
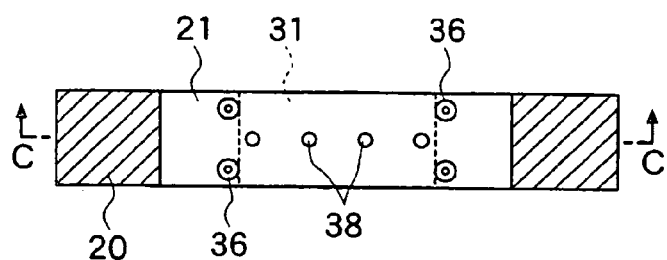
Figure 4:
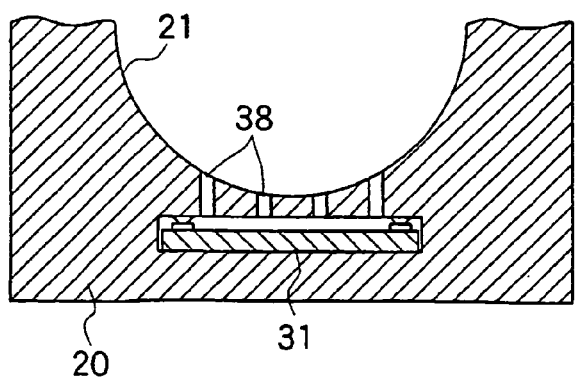
Figure 5:
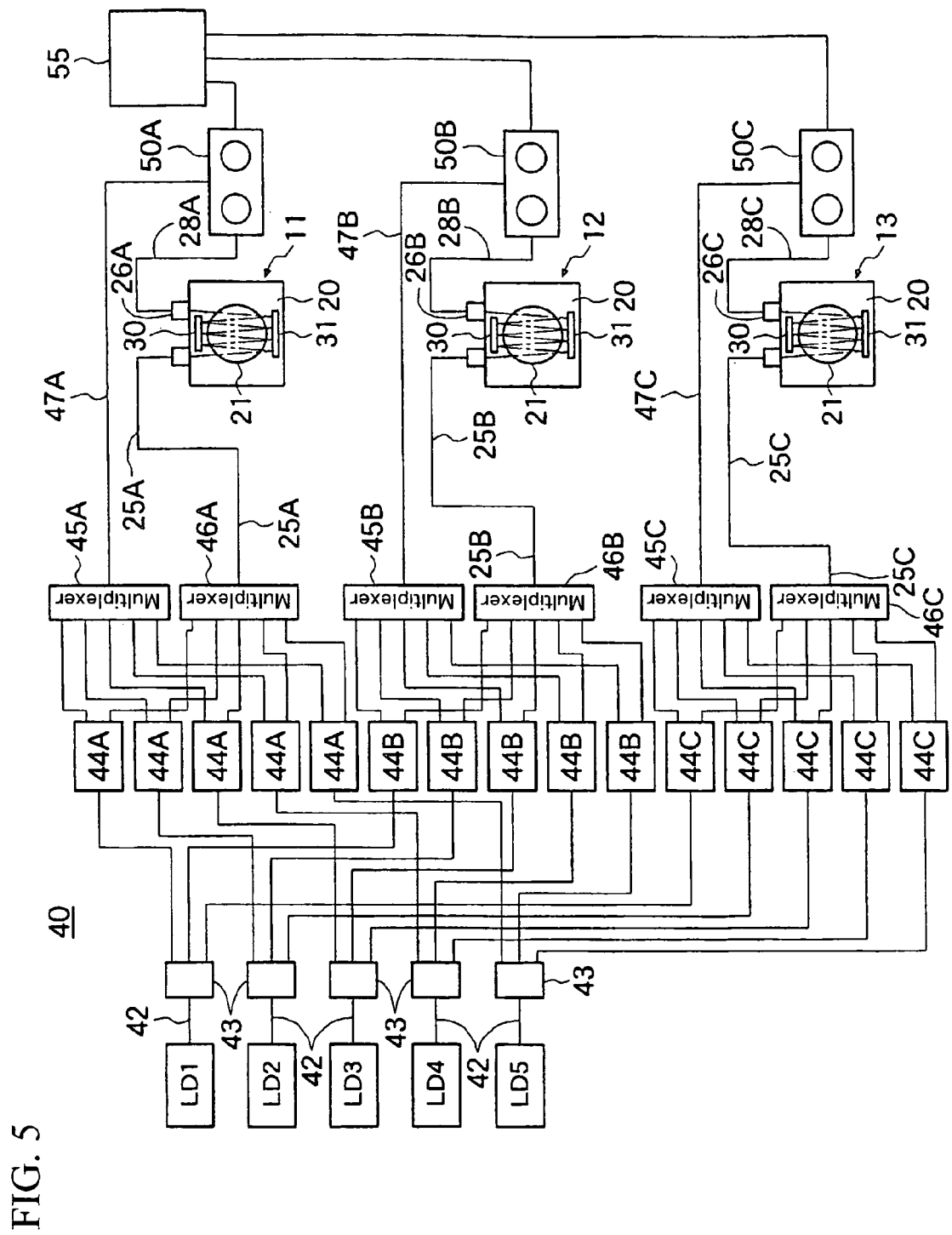
FIG. 5 is a block diagram showing the whole configuration of the exhaust gas analysis apparatus including the key component configuration of a laser oscillation/light reception controller and a signal analysis apparatus.

The two mirrors 30 and 31 are attached outside the circular exhaust gas venthole 21, which is located at the center of the sensor base 20, on opposite sides of the exhaust gas venthole, as shown in detail in FIG. 4. The two mirrors are disposed in such a way that the reflective surfaces of the mirrors are parallel to each other and secured in the upper and lower portions to reflect the measurement laser beam. That is, the mirrors 30 and 31 are disposed outside the exhaust gas venthole 21 and parallel to each other on opposite sides of the exhaust gas venthole. The mirrors 30 and 31 are removably secured in two insertion grooves 32 and 33 formed outside the exhaust gas venthole 21 and parallel to each other. The mirrors 30 and 31 have a function of guiding the laser beam, emitted from the optical fiber 25A toward the exhaust gas venthole 21, to the detector 26A. Each of the mirrors 30 and 31 is a rectangular substrate having a thickness on the order of a few millimeters, and has a thin film made of gold or platinum formed on one side of the substrate as the reflective surface. As a protective layer, a thin film made of $MgF_2$ or $SiO_2$ is formed on the reflective surface. It is noted that the protective layer may be omitted.

The insertion grooves 32 and 33 formed outside the exhaust gas venthole 21 in the sensor base 20 are sized in such a way that the mirrors 30 and 31 can be loosely inserted. The insertion grooves 32 and 33 may be open to both sides through the sensor base 20, or may be open to one side and closed on the other side. The mirrors 30 and 31 are secured in the insertion grooves 32 and 33 with securing screws 36 via spacers 37. In case the mirror gets broken due to thermal shock or the like, the broken mirror can be removed by loosening the securing screws 36 and replaced with a new one. When the mirror is contaminated, the mirror can be removed from the sensor base 20 for cleaning.

Since the mirrors 30 and 31 are secured with the securing screws 36 via the spacers 37, the mirrors will not vibrate due to the vibration of the engine and/or the vibration of the exhaust path, such as the exhaust duct. The spacer 37 is interposed to accommodate the difference in thermal expansion between the mirror and the securing screw and hence functions as a shock absorber. The spacer preferably has excellent resistance to environmental deterioration and elastically deforms. For example, the spacer is preferably formed of a mica-based or carbon-based plate or a copper plate. By thus securing the mirrors with the securing screws via the spacers, the mirrors will not vibrate, but can be stably secured even at high temperatures, for example, at approximately 800° C.

Each of the mirrors 30 and 31 is fabricated by coating a reflective material on the surface of the base material, such as quartz, sapphire, and ceramics. The coating material is preferably selected from those having high reflectance at the laser wavelength, such as gold and titanium oxides. As the coating for protecting the reflective material, it is preferable to form a transparent coating having excellent resistance to heat and environmental deterioration, such as $SiO_2$, on the top surface. Use of a highly reflective mirror having excellent resistance to heat allows accurate measurement. When titanium oxide is used as the reflective material, it is not necessary to form a protective layer because titanium oxide alone has excellent resistance to environmental deterioration and is also effective as a photocatalyst in preventing contamination. Therefore, the mirror coated with titanium oxide is preferably used as it is for measurement.

Light ventholes are formed between the inner circumferential surface of the exhaust gas venthole 21 and the insertion grooves 32, 33, in which the mirrors are secured, in order to allow the measurement laser beam to reach the mirrors. The light venthole may be a through slit, a through light venthole or the like. In this embodiment, light ventholes 38, 38 . . . , each having a diameter on the order of a few millimeters and extending from the inner circumferential surface of the exhaust gas venthole 21 to the insertion grooves 32, 33, are formed in the direction perpendicular to the exhaust path. The light ventholes thus extends from the inner circumferential surface of the exhaust gas venthole 21 and reach the mirrors 30 and 31. In this configuration, when the measurement infrared laser beam is emitted from the optical fiber 25, which is the illuminator, and enters the exhaust gas venthole 21, the laser beam reaches the lower mirror 31 through the lower light venthole 38, is reflected upward off the lower mirror, reaches the upper mirror 30 through the upper light venthole 38, is reflected downward off the upper mirror, and is received by the detector 26 fixed in the upper portion after repeatedly reflected off the upper and lower mirrors.

The optical fiber 25A and the detector 26A are connected to the laser oscillation/light reception controller 40. The infrared laser beam emitted from the laser oscillation/light reception controller 40 passes through the optical fiber 25A and illuminates the exhaust gas venthole 21 in the sensor base 20. The infrared laser beam that has passed through the exhaust gas is received by the light receiving-side detector 26A, and inputted to the laser oscillation/light reception controller 40 through a signal line 28A. The intensity of the illumination light emitted from the optical fiber 25A, the intensity of the light transmitted through the exhaust gas and received by the detector 26A and the like are supplied to the personal computer 55, which is the analysis apparatus. The exhaust gas analysis apparatus 10 is thus formed of the plurality of sensor units 11 to 14, the laser oscillation/light reception controller 40, and the personal computer 55.

The laser oscillation/light reception controller 40 will now be described with reference to FIG. 5. The laser oscillation/light reception controller 40 serves as an illumination apparatus that emit a plurality of infrared laser beams having respective wavelengths, and supplies a plurality of signals having respective frequencies from a signal generator (not shown), such as a function generator, to a plurality of laser diodes LD1 to LD5. The laser diodes LD1 to LD5 then emit infrared laser beams having respective wavelengths corresponding to the above frequencies. The plurality of frequency signals outputted from the signal generator in the laser oscillation/light reception controller 40 are supplied to the laser diodes LD1 to LD5 and drive them to emit infrared laser beams, the wavelengths of which form successive wavelength bands, each containing the peak wavelength for a component gas to be detected. For example, LD1 emits light having a wavelength approximately ranging from 1300 to 1330 nm, and LD2 emits light having a wavelength approximately ranging from 1330 to 1360 nm.

The wavelengths of the infrared laser beams to be transmitted through the exhaust gas are set in such a way that they correspond to the exhaust gas components to be detected. To detect carbon monoxide (CO), carbon dioxide ($CO_2$), ammonia ($NH_3$), methane ($CH_4$), and water ($H_2O$), infrared laser beams having five wavelengths are used. For example, the wavelength suitable for detecting ammonia is 1530 nm. The wavelength suitable for detecting carbon monoxide is 1560 nm. The wavelength suitable for detecting carbon dioxide is 1570 nm. The wavelength suitable for detecting methane is 1680 nm. The wavelength suitable for detecting water is 1350 nm. To detect the concentration of any of other exhaust gas components, infrared laser beams having different wavelengths are used in correspondence to the number of the exhaust gas components. Different wavelengths are used in some cases to detect the gas concentration even for the same component, so that an appropriate wavelength may be selected from various wavelengths.

The infrared laser beam emitted from each of the laser diodes LD1 to LD5 is guided through an optical fiber 42 . . . to a demultiplexer 43 . . . , which demultiplexes the laser beam. The number of demultiplexed laser beams coincides with the number of sensor units. In FIG. 5, the laser beam emitted from each of the laser diodes LD1 to LD5 is demultiplexed into three in correspondence to the three sensor units 11 to 13. The laser beams produced by the demultiplexing operation in the demultiplexers 43 . . . are divided by demultiplexers 44A . . . 44B . . . , and 44C . . . into signal beams and measurement beams. The demultiplexers 44A . . . 44B . . . , and 44C . . . are dedicated to the sensor units 11, 12, and 13, respectively. The signal light beams produced by the dividing operation in the five demultiplexers 44A . . . dedicated to the sensor unit 11 are carried through optical fibers and multiplexed by a multiplexer 45A. The multiplexed signal light beam that covers the plurality of wavelength bands is guided through an optical fiber 47A to a differential optical detector 50A, which will be described later. On the other hand, the measurement light beams produced by the dividing operation in the five demultiplexers 44A . . . are carried through optical fibers and multiplexed by a multiplexer 46A. The multiplexed measurement light beam is guided through the optical fiber 25A to the illuminator of the sensor unit 11.

Similarly, the infrared laser beams produced by the demultiplexing operation in the demultiplexers 43 . . . are divided into signal light beams and measurement light beams by the five demultiplexers 44B . . . dedicated to the sensor unit 12. The signal light beams are multiplexed by a multiplexer 45B into a signal light beam that covers the plurality of wavelength bands, and the multiplexed signal light beam is guided through an optical fiber 47B to a differential optical detector 50B. The measurement light beams produced by the dividing operation in the five demultiplexers 44B . . . are multiplexed by a multiplexer 46B, and the multiplexed measurement light beam is guided through an optical fiber 25B to the illuminator of the sensor unit 12. Further, the infrared laser beams produced by the demultiplexing operation in the demultiplexers 43 . . . are divided into signal light beams and measurement light beams by the five demultiplexers 44C . . . dedicated to the sensor unit 13. The signal light beams are multiplexed by a multiplexer 45C into a signal light beam that covers the plurality of wavelength bands, and the multiplexed signal light beam is guided through an optical fiber 47C to a differential optical detector 50C. The measurement light beams produced by the dividing operation in the five demultiplexers 44C . . . are multiplexed by a multiplexer 46C, and the multiplexed measurement light beam is guided through an optical fiber 25C to the illuminator of the sensor unit 13.

Although FIG. 5 shows the three sensor units 11 to 13, more sensor units 14 . . . can be disposed. In this case, each of the demultiplexers 43 demultiplexes the infrared laser beam into more laser beams. More demultiplexers 44 . . . demultiplex the demultiplexed laser beams into signal light beams and measurement light beams. Each of the multiplexers 45 . . . multiplex the signal laser beams, and the multiplexed signal laser beam is guided to the corresponding one of the differential optical detector 50 . . . . Each of the multiplexers 46 . . . multiplex the measurement laser beams, and the multiplexed measurement laser beam is guided to the corresponding one of more sensor units 14 . . . .

The exhaust gas analysis apparatus 10 of this embodiment is configured in such a way that the measurement infrared laser beam is reflected off the mirrors 30 and 31 to travel a long distance through the exhaust gas and the measurement laser beam repeatedly reflected off the mirrors 30 and 31 is received by the detector. The receiving-side detectors 26A, 26B, and 26C connected to the light detectors of the sensor units 11 to 13 are connected to the differential optical detector 50A, 50B, and 50C in the laser oscillation/light reception controller 40 via signal lines 28A, 28B, and 28C. The signal light beams produced by the multiplexing operation in the multiplexers 45A, 45B, and 45C are guided through the optical fibers 47A, 47B, and 47C to the differential optical detectors 50A, 50B, and 50C.

Each of the three differential optical detectors 50A, 50B, and 50C is configured to calculate the difference between the transmitted laser beam that has been attenuated through the exhaust gas and the signal laser beam that has not passed through the exhaust gas. Each of the signal laser beams is inputted to a photodiode or the like and converted into an electric signal. The electric signal corresponding to the difference between the signal light beam and the measurement light beam calculated by the differential optical detector is amplified by, for example, a preamplifier (not shown) and inputted to the personal computer 55, which is the signal analysis apparatus, via an A-to-D converter. The personal computer 55 uses the inputted signal to calculate the concentration of any of the components contained in the exhaust gas as well as the temperature, pressure and the like of the exhaust gas so as to analyze the exhaust gas.

The exhaust gas analysis apparatus 10 of the present invention analyzes the exhaust gas, for example, by sending the infrared laser beam through the exhaust gas and calculating the concentration of any of the components of the exhaust gas based on the intensity of the incident light and the intensity of the transmitted light that has passed through the exhaust gas. That is, the concentration C of any of the components of the exhaust gas is calculated by using the following equation (1):

$$C = -\ln(I/I_0)/kL \tag{1}$$

where I is the intensity of the transmitted light, $I_0$ is the intensity of the incident light, k is the absorption rate, and L is the pass length of the transmitted. The concentration C of any of the components of the exhaust gas is therefore calculated based on the ratio of the intensity of the transmitted light (I) to the intensity of the incident light ($I_0$), which is the signal light, that is, the signal intensity ($I/I_0$). The intensity of the transmitted light I is outputted through each of the detectors 26A, 26B, and 26C, and the intensity of the incident light $I_0$ is outputted from each of the photoelectric converters, such as the photodiodes, in the differential optical detectors 50A, 50B, and 50C through the optical fibers 47A, 47B, and 47C. In this embodiment, the intensity of the signal light, which does not pass through the exhaust gas, is used as the intensity of the incident light $I_0$.

The operation of the thus configured exhaust gas analysis apparatus 10 of this embodiment will be described below. The exhaust gas analysis apparatus 10 is actuated when the engine is in operation. The exhaust gas flows discharged from the engine 2 are merged in the exhaust manifold 3, which is the exhaust path, introduced into the first catalytic converter 5 through the exhaust duct 4, further introduced into the second catalytic converter 6, and discharged through the muffler 7 and the exhaust pipe 8 to the atmosphere. In this process, the exhaust gas passes through the exhaust gas venthole 21 formed in the sensor base 20 of each of the sensor units 11 to 14 disposed along the exhaust path. To measure the concentration and the like of a specific component of the exhaust gas, the laser beam is applied to the exhaust gas venthole 21 and the light intensity of the laser beam that has passed through the exhaust gas is measured.

That is, the signal generator in the laser oscillation/light reception controller 40 is actuated to supply signals to the laser diodes LD1 to LD5, so that they emit infrared laser beams, each having a predetermined wavelength. The infrared laser beam emitted from each of the laser diodes LD1 to LD5 is carried through the optical fiber 42 to the demultiplexer 43 and demultiplexed in such a way that the number of demultiplexed laser beams coincides with the number of sensor units. Then, the demultiplexed infrared laser beams are further demultiplexed into measurement light beams and signal light beams by the demultiplexers 44A . . . , 44B . . . , and 44C . . . .

The following detailed description will be made with reference to one sensor unit 11. The signal light beams produced by the demultiplexing operation in the five demultiplexers 44A are multiplexed by the multiplexer 45A into a signal laser beam, which is guided to the differential optical detector 50A. The measurement light beams produced by the demultiplexing operation in the five demultiplexers 44A are multiplexed by the multiplexer 46A into a measurement laser beam, which is guided through the optical fiber 25A to the illuminator of the sensor unit 11. Similarly, for the other sensor units 12 and 13, the infrared laser beams are demultiplexed by the demultiplexers 43 . . . . The demultiplexed laser beams are further demultiplexed into signal light beams and measurement light beams by the demultiplexers 44B . . . and 44C . . . . The signal light beams are multiplexed by the multiplexers 45B and 45C and guided to the differential optical detectors 50B and 50C, and the measurement light beams are multiplexed by the multiplexers 46B and 46C and guided to the sensor units 12 and 13.

Then, the measurement infrared laser beam emitted from each of the optical fibers 25A, 25B, and 25C in the sensor units 11 to 13 is applied to the exhaust gas venthole 21, through which the exhaust gas passes, via the sensor hole 23, which is the illumination light venthole. The infrared laser beam passes across the exhaust gas venthole 21, which is the exhaust path, reaches the mirror 31 through the light venthole 38, is reflected upward off the lower mirror 31, reaches the mirror 31 through the light venthole 38, and is reflected downward off the upper mirror 30. Such reflection is repeated so that the pass length of the transmitted light through the exhaust gas increases. Finally, the infrared laser beam passes through the sensor hole 24 and is detected by each of the detectors 26A, 26B, and 26C. That is, the measurement infrared laser beam is attenuated through the exhaust gas, and the attenuated, transmitted light is received by the detector, which is the light detector. The intensity of the transmitted light (measurement light) is then measured.

The measurement infrared laser beams that have been attenuated through the exhaust gas and reached the light detectors are outputted as electric signals from the detectors 26A, 26B, and 26C, and the outputted electrical signals are supplied to the differential optical detector 50A, 50B, and 50C through the signal lines 28A, 28B, and 28C. On the other hand, the signal laser beams are supplied to the differential optical detector 50A, 50B, and 50C, each of which then calculates the difference between the transmitted light (measurement light) and the signal light for each of the plurality of wavelength components, and detects the absorption spectrum from which the peak wavelength for a specific gas component has been detected in the transmitted light. The outputs from the differential optical detectors are inputted to the personal computer 55, which is the signal analysis apparatus. Based on the peak wavelength for each of the plurality of frequency bands in the inputted absorption spectrum, the personal computer 55 calculates, measures, and analyzes the concentration, temperature, and pressure of the corresponding component of the exhaust gas.

Figure 6:
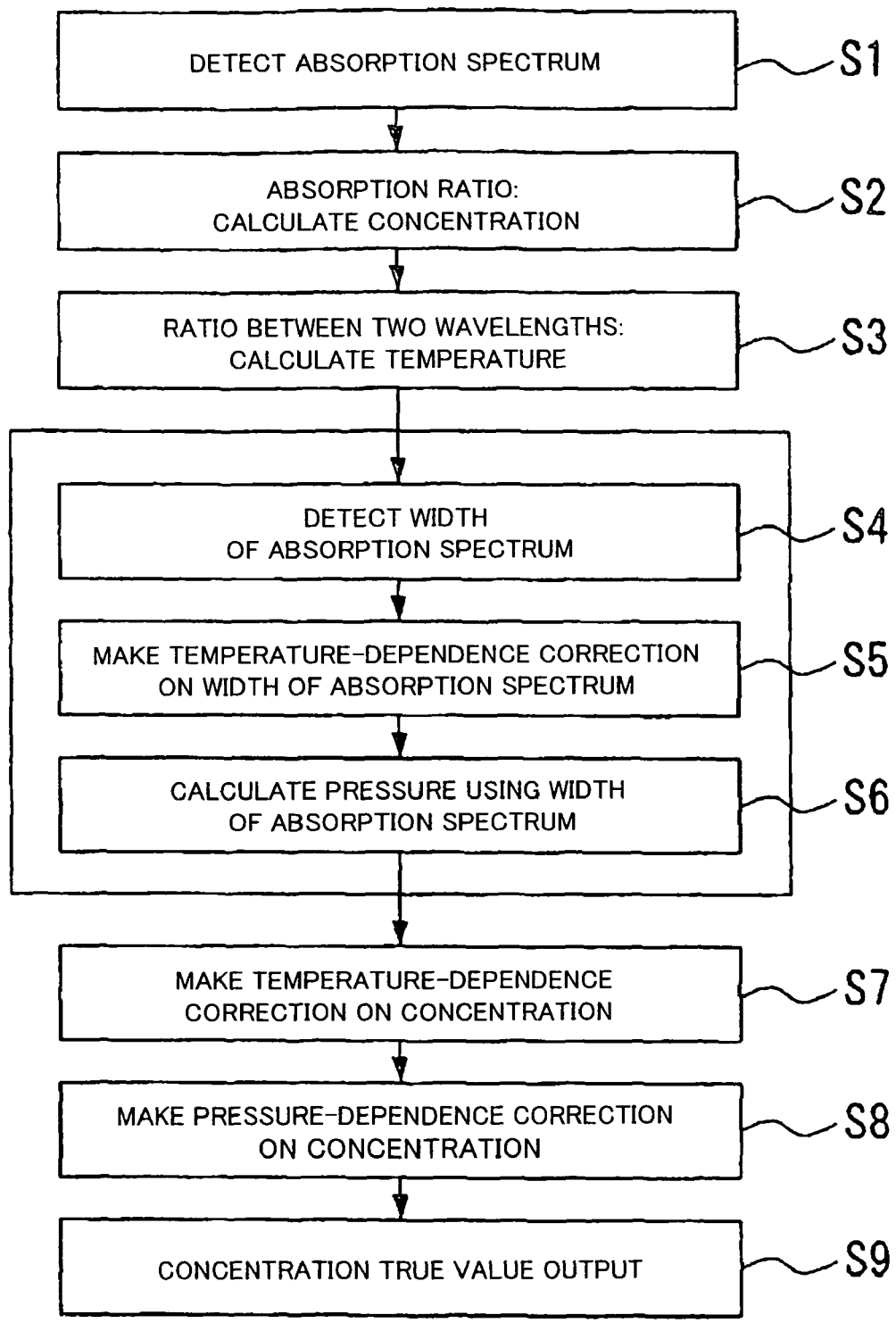
FIG. 6 is a flowchart showing the steps of the exhaust gas analysis method according to the present invention.

The exhaust gas analysis apparatus 10 of this embodiment analyzes the exhaust gas by processing the thus obtained absorption spectrum of the transmitted laser beam according to the flowchart shown in FIG. 6. In the step S1, the measurement laser beam that has passed through the exhaust gas and the signal laser beam that has not passed through the exhaust gas are inputted to the differential optical detector to detect the absorption spectrum. Then, the ratio of the light intensity I of the measurement laser beam that has passed through the exhaust gas to the light intensity $I_0$ of the signal laser beam that has not passed through the exhaust gas is used to calculate the concentration of a specific component of the exhaust gas (step S2). This calculation is carried out by using the equation (1) described above.

Figure 7:
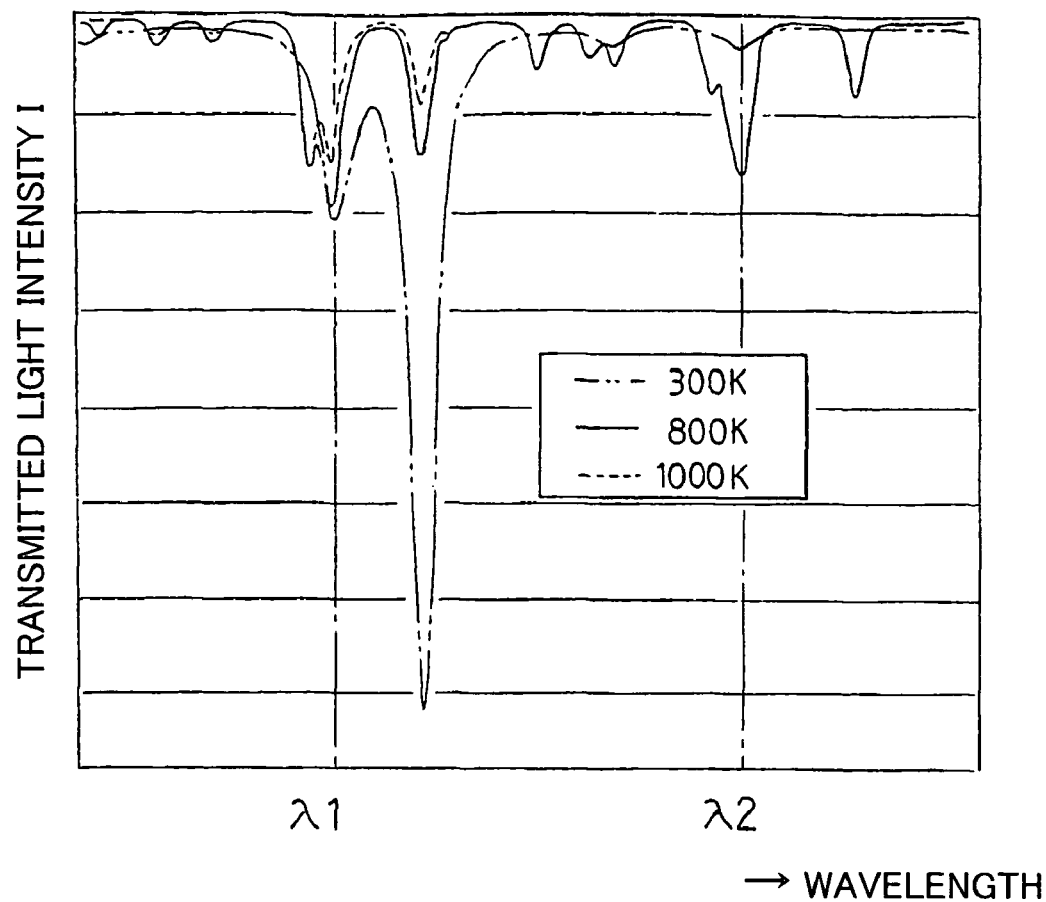
FIG. 7 shows how the temperature affects the absorption spectrum and explains how the absorption spectrum changes with temperature.

Then, the calculated gas concentration of the characteristic component is corrected. First, in the step S3, the temperature of the exhaust gas is calculated to make temperature-dependence correction. That is, the ratio between two specific wavelengths in the absorption spectrum detected in the step S1 is used to calculate and measure the temperature of the flowing exhaust gas. The calculation of the temperature of the exhaust gas is carried out as follows: Every gas has its unique absorption wavelength band, in which a large number of absorption lines are present, as shown in FIG. 7. FIG. 7 shows signal intensities (=proportion of the number of molecules) at 300 K, 800 K, and 1000 K. Since the signal intensity thus varies with the temperature, by measuring the signal intensity ratio, the temperature of the exhaust gas at the time of measurement can be calculated.

That is, it has been known that the intensity of the transmitted light that has passed through the exhaust gas changes with the concentration, temperature, and pressure of the exhaust gas, but the ratio between the transmitted light intensities I at two specific wavelengths is not affected by the concentration nor the pressure but depends on the temperature. Therefore, the $H_2O$ concentrations C1 and C2 at specific $\lambda 1$ and $\lambda 2$ can be calculated by using the equation (1) described above, and the fact that the two concentration values are the same can be used to calculate the temperature in the equation for calculating the concentration. Specifically, the absorption rate k in the equation (1) is expressed by the product of the absorption line intensity S(T) and the gas pressure Pabs, that is, k=S(T)×Pabs. The absorption line intensity S(T) is expressed as follows: $S(T)=\alpha \times (Na/RT)$, where $\alpha$ is the absorption rate cross-sectional area, Na is the Avogadro number, R is the gas constant, and T is the temperature. $H_2O$ (water vapor), which is always present in the exhaust gas, is suitably used in the temperature calculation. In FIG. 7, the measurement is carried out by using the wavelength band around 1379 nm as the modulation range, and the vertical axis is defined in such a way that the transmitted light intensity increases in the downward direction. The exhaust gas temperature is not necessarily calculated by using two specific wavelengths, but may be calculated by using at least two selected wavelengths.

Then, to make pressure-dependence correction, in the steps S4 to S6 boxed with the solid-line rectangle in FIG. 6, the pressure of the exhaust gas is calculated. The steps in the solid-line rectangle have been conventionally carried out by using a pressure sensor disposed in the exhaust path to measure the pressure. In this embodiment, however, the pressure is calculated based on the detected absorption spectrum without using a pressure sensor. The configuration is therefore simplified because the pressure sensor can be omitted, and the calculated pressure can be used to correct the concentration in realtime. $H_2O$, that is, water vapor, which is always present in the exhaust path to be measured, is preferably used as the specific gas component used in the pressure calculation.

Figure 8:
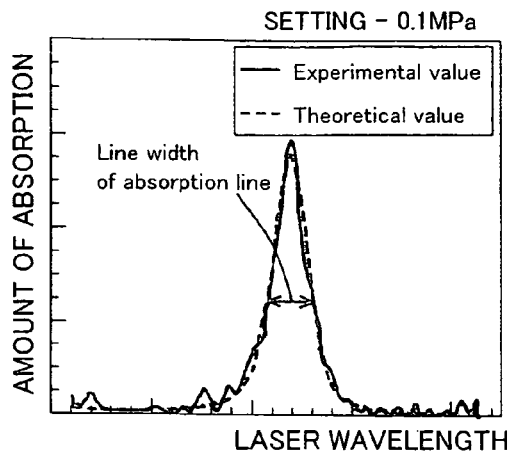
FIGS. 8(a), 8(b), 8(c), and 8(d) are explanatory views showing peak values and spectrum widths of the absorption spectrum and the theoretical spectrum at respective pressures differently set.
Figure 8:
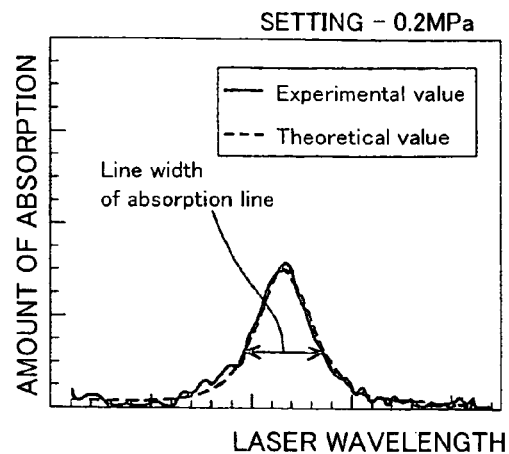
Figure 8:
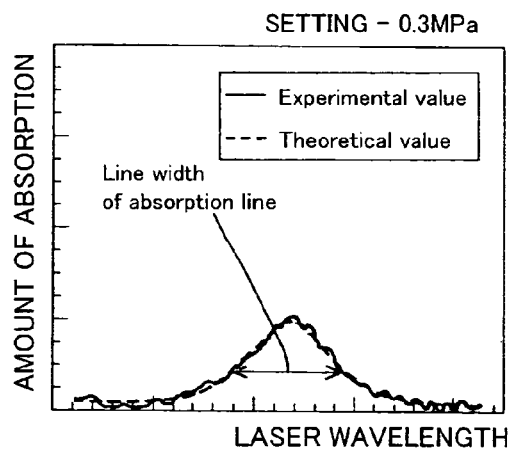
Figure 8:
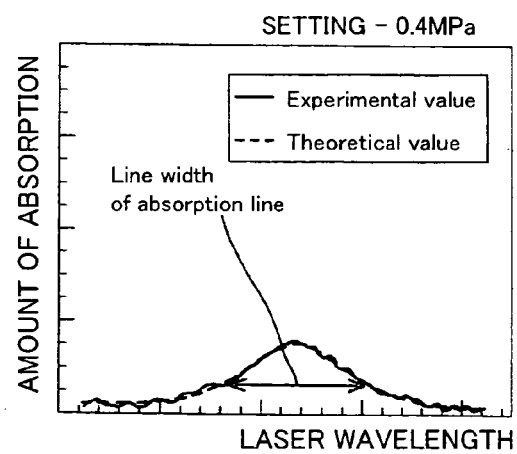

The pressure calculation using the absorption spectrum is carried out by using the full width at half maximum of the $H_2O$ absorption spectrum. That is, as shown in FIG. 8, the shape of the absorption spectrum changes with pressure. Specifically, as the pressure becomes higher, the peak portion collapses and the shape becomes flatter. Therefore, the flatness is approximated by the full width at half maximum to calculate the pressure. In the step S4, the width (full width at half maximum) of the absorption spectrum is detected. Then, in the step S5, the width of the absorption spectrum is corrected based on the temperature of the exhaust gas calculated in the step S3. This correction is carried out by using the correction curve shown in FIG. 9(a). To make correction, the amount of line width correction corresponding to the temperature on the horizontal axis is multiplied. Based on the thus corrected spectrum width, the diagram shown in FIG. 9(b) can be used to calculate the pressure (step S6).

In this embodiment, since the pressure is calculated from the shape of the absorption spectrum without using a pressure sensor, pressure data on the exhaust gas can be obtained in realtime. Then, in the step S7, the temperature data calculated in the step S3 is used to correct the concentration calculated in the step S2. In the step S8, the pressure data calculated in the step S6 is used to further correct the concentration corrected in the preceding step. The correction operations in the steps S8 and S9 are, in practice, carried out simultaneously. The theoretical spectrum is corrected by substituting the actually calculated temperature and pressure values in the temperature and pressure terms in a theoretical equation for determining the theoretical spectrum. The relation between the result of the correction and the absorption spectrum actually measured and detected can be used to determine the true concentration.

Specifically, numerical values are substituted in the temperature and pressure terms in the following equation (2) to correct the theoretical spectrum. That is, it has been known that, in general, the spectrum of the light emitted from a molecule will not be a pure line spectrum but a broadened one. The broadening is categorized into three types: spontaneous broadening, collision broadening, and Doppler broadening. The spontaneous broadening results from the uncertainty of the molecular energy. The collision broadening results from disturbed molecular vibration due to molecule-molecule collision. The Doppler broadening results from the Doppler effect between the molecule translation and light.

By formulating an equation for calculating the theoretical spectrum at a predetermined temperature, pressure, and gas concentration in consideration of the three broadening, the following equation (2), called the Voigt function, is obtained:

[Formula 1]

Voigt function (2)

$$I_\lambda = \frac{2}{\pi} \cdot \frac{\lambda_c}{W_L} Adbs \int \frac{\exp\left(-\frac{2.772\lambda_c^2}{W_g^2}X^2\right)^2}{1+[(\lambda-\lambda_c)-X\lambda_c]^2} dX$$

where $I_\lambda$ is the amount of absorption at the wavelength $\lambda$, $\lambda_c$ is the absorption line wavelength, Adsb is the amount of light absorption at the absorption line, $W_L$ is the full width half maximum of the pressure broadening, and $W_g$ is the full width half maximum of the temperature broadening.

Adbs=[1−exp(−α×N×L)]

where α is the absorption rate, L is the pass length of transmitted, and N is the number of molecules.

$W_L = P \times (294/T)^{a1}$, $W_g = b1 \times T^{a2}$ where T is the temperature, P is the pressure, and a1, a2, and b1 are molecule-related coefficients. In the concentration correction operations in the steps S7 and S8, the theoretical spectrum is corrected by substituting the temperature calculated in the step S3 and the pressure calculated in the step S6 in the temperature and pressure terms in the equation (2). The true value of the concentration is then outputted in the step S9.

The computation and signal analysis according to the above flowchart are carried out based on the data and equations stored in the memory in the personal computer 55, and the calculated values are corrected. The results are outputted and displayed on an accompanying display. That is, in the analysis of the exhaust gas, the true gas concentration for each of specific gas components in the exhaust gas is displayed on the display of the personal computer 55 for each of the plurality of sensor units 11 to 14. As described above, the differential optical detector 50 forms the detection means for detecting the absorption spectrum from the received laser beam, and the personal computer 55 not only forms the calculation means for calculating the concentration of the exhaust gas, calculating the temperature of the exhaust gas from the absorption spectrum, and calculating the pressure of the exhaust gas from the absorption spectrum, but also forms the correction means for correcting the calculated gas concentration.

Figure 9:
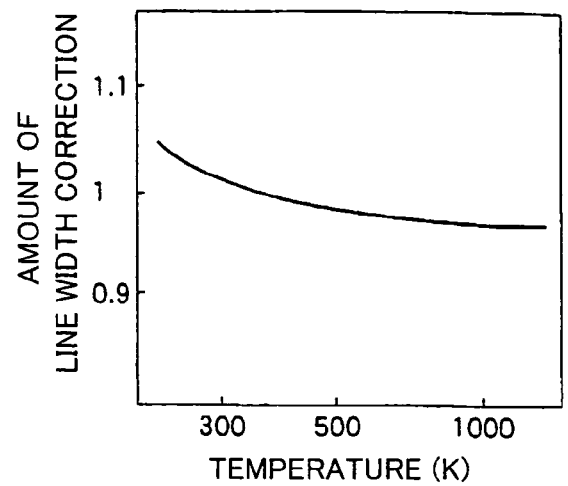
FIGS. 9(a) to 9(c) are correction diagrams used in the flowchart in FIG. 6.
Figure 9:
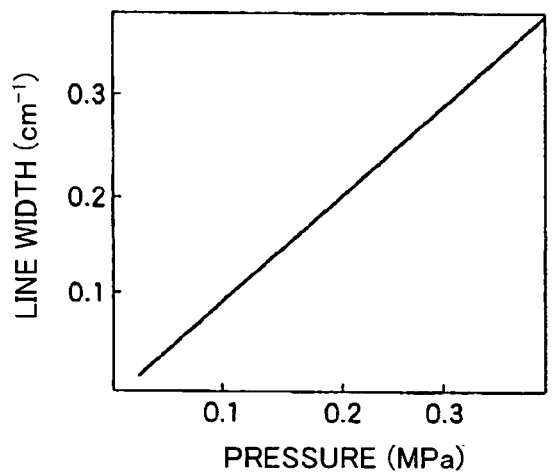
Figure 9:
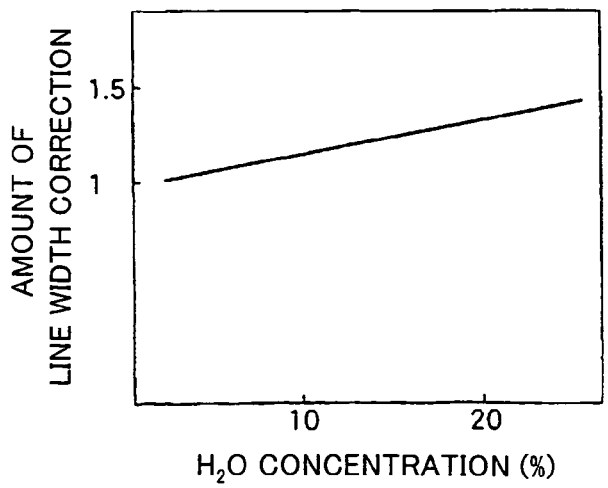

Although not illustrated, in the flowchart shown in FIG. 6, the step of making concentration-dependence correction on the width of the absorption spectrum may be inserted between the steps S4 and S5. In this case, based on the $H_2O$ concentration calculated in the step S2, the correction diagram shown in FIG. 9(c) is used to determine the amount of line width correction, and the width of the absorption spectrum detected in the step S4 is multiplied by the amount of correction determined above for correction. This step is also carried out in the personal computer 55 as part of a series of computation.

Figure 10:
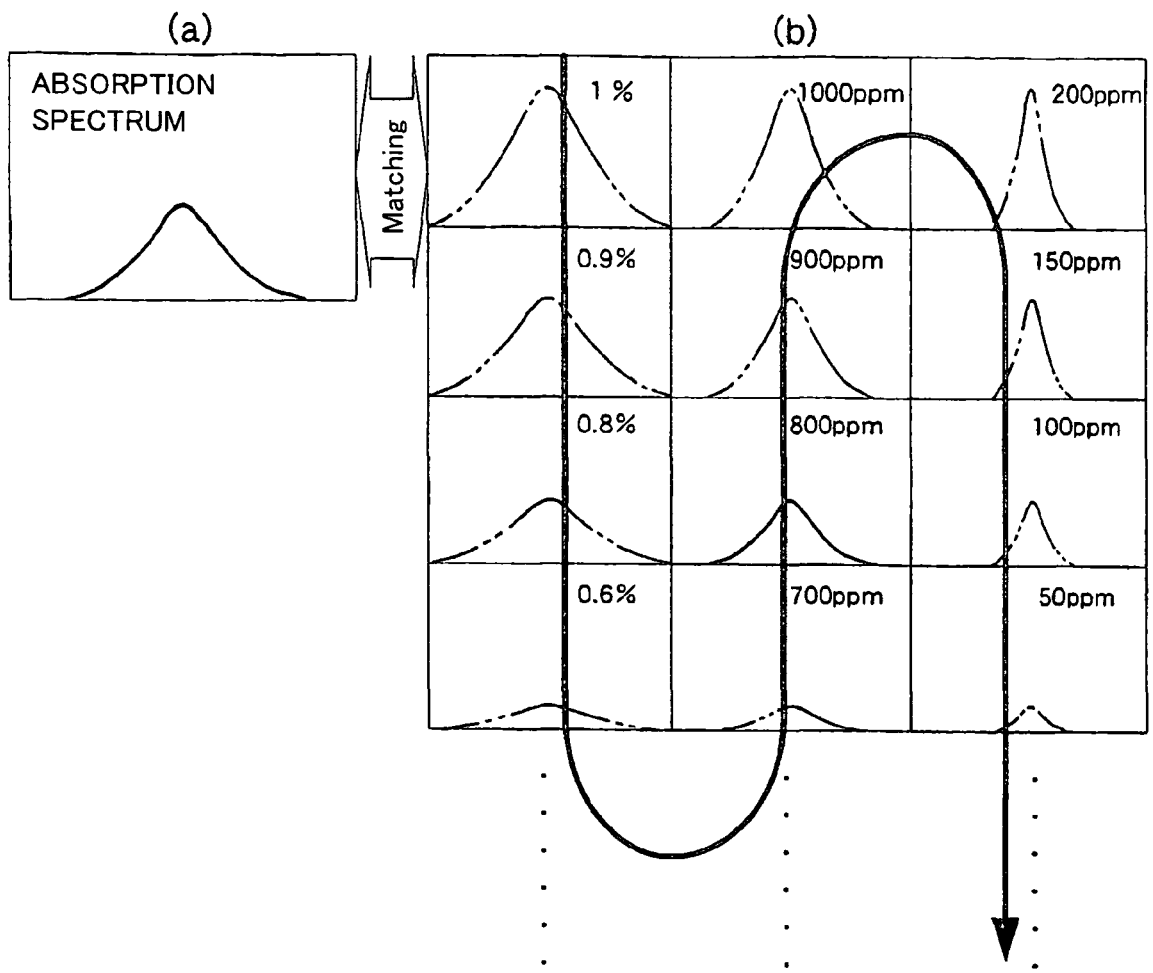
FIG. 10 explains how the pressure is calculated from the absorption spectrum in another embodiment of the exhaust gas analysis method according to the present invention.

Another embodiment of the present invention will be described with reference to FIG. 10. FIG. 10 explains how a detected absorption spectrum is used to calculate the gas concentration of a specific component in the exhaust gas at the time of detection. This embodiment is carried out instead of calculating the pressure in the steps S4 to S6 in the flowchart (FIG. 6) used in the embodiment described above. That is, the concentration of the exhaust gas is calculated by detecting the absorption spectrum in the step S1, calculating the concentration from the absorption ratio obtained from the absorption spectrum in the step S2, calculating the temperature of the exhaust gas from the ratio between two wavelengths in the step S3, and using a pattern matching-based fitting method, which will be described with reference to FIG. 10.

To calculate the pressure using this method, the shapes of a large number of pre-calculated theoretical spectra shown in (b) are compared with the shape of the absorption spectrum shown in (a) detected in the step S1 so as to determine the nearest approximate spectrum. The concentration is then determined based on this spectrum. In the illustrated example, the pre-calculated theoretical spectra for gas concentrations of 1%, 0.9%, 0.8% . . . , 1000 PPM, 900 PPM, 800 PPM . . . , 200 PPM, 150 PPM, 100 PPM, 50 PPM . . . are compared with the shape of the measured absorption spectrum so as to select the theoretical spectrum having the nearest shape and determine the gas concentration at the time of measurement. Such calculation of the gas concentration causes a problem of increase in analysis time, which can, however, be addressed by increasing the processing power of the arithmetic processor.

Figure 11:
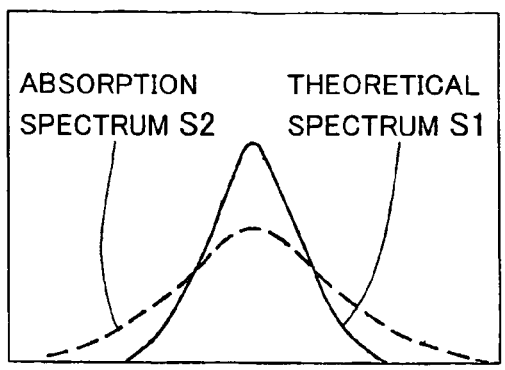
FIG. 11 explains how the gas concentration is corrected in still another embodiment of the exhaust gas analysis method according to the present invention.
Figure 11:
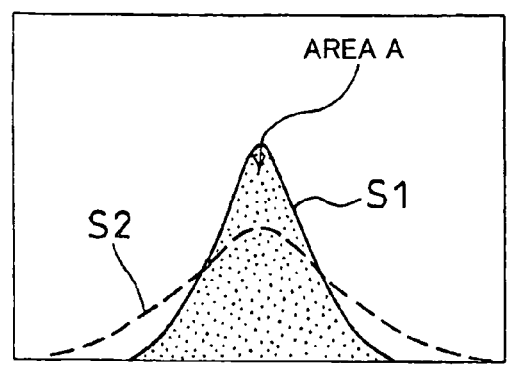
Figure 11:
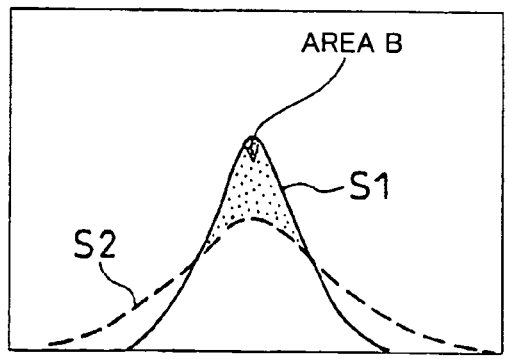
Figure 11:
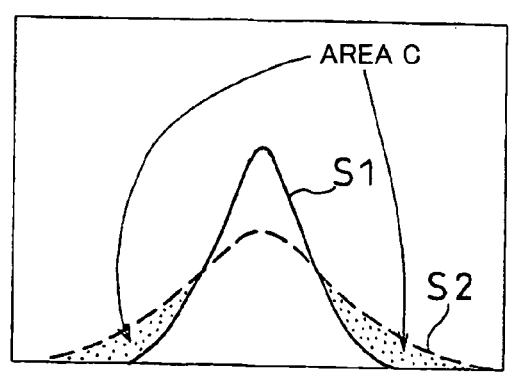

Still another embodiment of the present invention will be described with reference to FIG. 11. FIG. 11 explains how the gas concentration is corrected by using a detected absorption spectrum. In FIG. 11, the horizontal axis represents the wavelength and the vertical axis represents the light intensity. This embodiment is characterized in that the true concentration value is outputted by correcting the gas concentration calculated in the step S2 in the flowchart (FIG. 6) used in the embodiment described above. That is, this embodiment, which outputs the true concentration value by correcting the concentration, includes the step of comparing the absorption spectrum detected in the step S1 with the theoretical spectrum uniquely determined by the concentration calculated in the step S2, the temperature calculated in the step S3, and the pressure calculated in the steps S4 to S6 so as to calculate a concentration correction value instead of executing the steps S7 and S8, and the step of correcting the concentration by using the calculated correction value.

In this embodiment, as shown in (a), the theoretical spectrum S1 is superimposed on the absorption spectrum S2, and the integral of the theoretical spectrum (first area A) is first calculated. Then, the integral (second area B) of the portion where the value of the theoretical spectrum S1 is larger than that of the absorption spectrum S2, and the integral (third area C) of the portion where the value of the absorption spectrum S2 is larger than that of the theoretical spectrum S1 are calculated. Based on the thus calculated three areas A, B, and C, the following equation (3) is used to calculate the correction value x. That is, $$\text{Correction value } x = (\text{First area } A - \text{Second area } B + \text{Third area } C)/\text{First area } A \quad (3)$$

Therefore, when the second area B is equal to the third area C, the correction value x becomes "1".

By thus calculating the concentration correction value x and multiplying the gas concentration corresponding to the area A of the theoretical spectrum described above by the correction value x, the true gas concentration value can be obtained. The true gas concentration value is calculated by using the following equation (4). That is, $$\text{True gas concentration value} = \text{Area of theoretical spectrum } S1 (\text{First area } A) \times \text{Correction value } x \quad (4)$$

In this embodiment, since the gas concentration calculated from the shape of the theoretical spectrum is corrected by calculating the correction value based on the shapes of the theoretical spectrum and the absorption spectrum, the computation time for obtaining the true gas concentration value can be substantially reduced. As a result, the exhaust gas analysis can be quickly carried out, which contributes to the exhaust gas analysis in the development of an engine and the like. These computing operations are carried out in the personal computer 55. In this embodiment, since the gas concentration is corrected by computing the correction value without carrying out the pattern matching unlike the embodiment described above, it is possible to improve the calculation speed and hence measure the gas concentration in realtime.

Although the embodiments of the present invention have been described above in detail, the present invention is not limited thereto, but various design changes can be made to the extent that they do not depart from the spirit of the present invention set forth in the claims. For example, although there have been illustrated several examples of the calculation of the concentration of any of the components of the exhaust gas, including the calculation by using the equation (1), the calculation by determining the area of the shape of the absorption spectrum, and the calculation by comparing the shape of the absorption spectrum with the shape of the theoretical spectrum uniquely determined by the temperature, the pressure, and the gas concentration and performing pattern matching to determine the gas concentration, other methods may be used to calculate the gas concentration.

Further, the configuration of the sensor unit is presented by way of example, but not limited to the configuration described above. For example, the laser beam illuminator and the laser beam receiver may be disposed on opposite sides of the gas venthole, and the laser beam may be directly received using no reflective member, such as a mirror. Alternatively, one mirror is used to reflect the laser beam emitted from the illuminator only once and the reflected light is then received.

Further, the mirror may have a photocatalyst layer formed thereon, the photocatalyst layer formed of, for example, a thin film made of titanium oxide ($TiO_2$). The thin film serves to absorb light rays, such as ultraviolet light, which activate the photocatalyst, so that contaminants attached to the surface float. Then, the flow of the exhaust gas carries the floating contaminants and discharges them from the exhaust path to the outside. Therefore, the surface of the mirror can be cleaned and hence the reflectance thereof can be enhanced in a preferred manner.

INDUSTRIAL APPLICABILITY

As applications of the present invention, the exhaust gas analysis apparatus can be used to analyze the exhaust gas from a combustion apparatus, such as a boiler, or can be applied to the analysis of the exhaust gas from an internal combustion engine used in a ship and a generator as well as the analysis of the exhaust gas from an automobile. Further, it is possible to analyze the exhaust gas from a diesel engine as well as the exhaust gas from a gasoline engine. Moreover, the exhaust gas analysis apparatus can be applied to the analysis of the exhaust gas from other types of internal combustion engines.

The invention claimed is:
1. An exhaust gas analysis method, comprising:
applying a laser beam from a laser beam generator of an exhaust gas analysis apparatus to the exhaust gas discharged from an internal combustion engine;
receiving, at a laser beam receiver of the exhaust gas analysis apparatus, the laser beam that has passed through the exhaust gas; and
measuring a concentration of any of the components contained in the exhaust gas based on the received laser beam,
wherein the measuring comprises:
detecting an absorption spectrum of the laser beam absorbed in the exhaust gas by using the received laser beam,
calculating the concentration of the component contained in the exhaust gas, the temperature of the exhaust gas, and the pressure of the exhaust gas by using the absorption spectrum without using a pressure sensor, wherein the exhaust gas temperature is calculated from the ratio between the transmitted light intensities at least two wavelengths selected from the absorption spectrum for $H_2O$, wherein the exhaust gas pressure is calculated based on the spectrum width at the peak wavelength in the absorption spectrum for $H_2O$, and
correcting the calculated concentration of the component contained in the exhaust gas by using the calculated exhaust gas temperature and the calculated exhaust gas pressure,
wherein the measuring is performed by the exhaust gas analysis apparatus.

2. An exhaust gas analysis method, comprising:
applying a laser beam from a laser beam generator of an exhaust gas analysis apparatus to the exhaust gas discharged from an internal combustion engine;
receiving, at a laser beam receiver of the exhaust gas analysis apparatus, the laser beam that has passed through the exhaust gas; and
measuring a concentration of any of the components contained in the exhaust gas based on the received laser beam,
wherein the measuring comprises:
detecting an absorption spectrum of the laser beam absorbed in the exhaust gas by using the received laser beam;
calculating the concentration of the component contained in the exhaust gas, the temperature of the exhaust gas, and the pressure of the exhaust gas by using the absorption spectrum without using a pressure sensor;
calculating a concentration correction value based on not only a theoretical spectrum determined by the exhaust gas temperature, the exhaust gas pressure, and the concentration of the component contained in the exhaust gas that have been calculated from the absorption spectrum but also the detected absorption spectrum, wherein the exhaust gas temperature is calculated from the ratio between the transmitted light intensities at least two wavelengths selected from the absorption spectrum for $H_2O$, wherein the exhaust gas pressure is calculated based on the spectrum width at the peak wavelength in the absorption spectrum for $H_2O$; and
correcting the calculated concentration of the component contained in the exhaust gas by using the correction value,
wherein the measuring is performed by the exhaust gas analysis apparatus.

3. The exhaust gas analysis method according to claims 1 or 2, wherein the calculation of the concentration of the component contained in the exhaust gas comprises preparing a plurality of spectrum patterns obtained by changing the theoretical spectrum of the specific component of the exhaust gas to be analyzed according to the concentration of the component, and calculating the concentration from the exhaust gas concentration for the nearest approximate spectrum pattern.

4. An exhaust gas analysis apparatus that applies a laser beam generated in laser beam generation means to the exhaust gas discharged from an internal combustion engine, receives the laser beam that has passed through the exhaust gas, and measures the concentration of any of the components contained in the exhaust gas based on the received laser beam, comprising:
detection means for detecting an absorption spectrum of the laser beam absorbed in the exhaust gas by using the received laser beam;
calculation means for calculating the concentration of the component contained in the exhaust gas, the temperature of the exhaust gas, and the pressure of the exhaust gas by using the absorption spectrum, wherein the exhaust gas temperature is calculated from the ratio between the transmitted light intensities at least two wavelengths selected from the absorption spectrum for $H_2O$, wherein the exhaust gas pressure is calculated based on the spectrum width at the peak wavelength in the absorption spectrum for $H_2O$; and
correction means for correcting the calculated concentration of the component contained in the exhaust gas by using the calculated exhaust gas temperature and the calculated exhaust gas pressure,
wherein the exhaust gas analysis apparatus lacks a pressure sensor.

5. An exhaust gas analysis apparatus that applies a laser beam generated in laser beam generation means to the exhaust gas discharged from an internal combustion engine, receives the laser beam that has passed through the exhaust gas, and measures the concentration of any of the components contained in the exhaust gas based on the received laser beam, comprising:
detection means for detecting an absorption spectrum of the laser beam absorbed in the exhaust gas by using the received laser beam;
calculation means for calculating the concentration of the component contained in the exhaust gas, the temperature of the exhaust gas, and the pressure of the exhaust gas by using the absorption spectrum, wherein the exhaust gas temperature is calculated from the ratio between the transmitted light intensities at least two wavelengths selected from the absorption spectrum for $H_2O$, wherein the exhaust gas pressure is calculated based on the spectrum width at the peak wavelength in the absorption spectrum for $H_2O$,
the calculation means further calculating a concentration correction value based on not only a theoretical spectrum determined by the calculated exhaust gas temperature, exhaust gas pressure, and concentration of the component of the exhaust gas but also the detected absorption spectrum; and
correction means for correcting the calculated concentration of the component contained in the exhaust gas by using the correction value,
wherein the exhaust gas analysis apparatus lacks a pressure sensor.

* * * * *